US007709796B2

(12) United States Patent
Gorian et al.

(10) Patent No.: US 7,709,796 B2
(45) Date of Patent: May 4, 2010

(54) METHODS AND SYSTEMS FOR DETECTING PRESENCE OF MATERIALS

(75) Inventors: Izrail Gorian, Watertown, MA (US); Lev Z. Vilenchick, Waltham, MA (US); Galina Doubinina, Watertown, MA (US)

(73) Assignee: Iscon Video Imaging, Inc., Watertown, MA (US)

( * ) Notice: Subject to any disclaimer, the term of this patent is extended or adjusted under 35 U.S.C. 154(b) by 364 days.

(21) Appl. No.: 11/348,121

(22) Filed: Feb. 6, 2006

(65) Prior Publication Data

US 2009/0202128 A1    Aug. 13, 2009

Related U.S. Application Data

(60) Provisional application No. 60/593,950, filed on Feb. 25, 2005.

(51) Int. Cl.
*G01J 5/02* (2006.01)
*G01N 21/00* (2006.01)
*G01N 21/35* (2006.01)

(52) U.S. Cl. .............. 250/339.01; 250/339.07; 250/342; 382/190; 382/191; 382/203

(58) Field of Classification Search .......... 250/339.07–339.08; 356/300–301; 382/156, 382/190, 191, 195, 203
See application file for complete search history.

(56) References Cited

U.S. PATENT DOCUMENTS

| 5,073,782 | A |  | 12/1991 | Huguenin et al. ........... 342/179 |
| 5,804,448 | A | * | 9/1998 | Wang et al. .................. 436/63 |
| 6,216,540 | B1 |  | 4/2001 | Nelson et al. ................. 73/633 |
| 6,716,638 | B1 |  | 4/2004 | Hsiung ...................... 436/147 |
| 6,751,342 | B2 |  | 6/2004 | Shepard ..................... 382/141 |
| 6,876,322 | B2 |  | 4/2005 | Keller ........................ 342/22 |
| 6,887,711 | B1 | * | 5/2005 | Diem et al. .................. 436/63 |
| 7,289,233 | B2 | * | 10/2007 | Kurokawa et al. ........... 356/630 |
| 2002/0113210 | A1 |  | 8/2002 | Treado et al. ............... 250/331 |
| 2002/0123977 | A1 | * | 9/2002 | Raz ............................ 706/15 |
| 2005/0017179 | A1 | * | 1/2005 | Mordechai et al. ..... 250/339.08 |

OTHER PUBLICATIONS

Brooks, R. R., L. Grewe, and S. S. Iyengar, "Recognition in the Wavelet Domain: A Survey," Journal of Electronic Imaging 10 (3), Jul. 2001: 757-784.*
Chen, Z., T. J. Feng and Z. Houkes, "Texture Segmentation based on Wavelet and Kohonen Network for Remotely Sensed Images," IEEE SMC '99 IEEE Conference Proceedings: vol. 6, p. 816-821.*
Singh, S. and M. Singh, "Explosives Detection Systems (EDS) for Aviation Security," Signal processing 83 (2003): 31-55.*
Weldon et al. Gabor filter design for multiple texture segmentation. Optical Engineering, vol. 35, No. 10, pp. 1-17, Oct. 1996.

* cited by examiner

*Primary Examiner*—David P Porta
*Assistant Examiner*—Casey Bryant
(74) *Attorney, Agent, or Firm*—Burns & Levinson LLP; Orlando Lopez

(57) ABSTRACT

Methods and systems for detecting the presence of concealed objects.

50 Claims, 11 Drawing Sheets

Structural Diagram of the proposed system

Structural Diagram of the proposed system

Front View   Side View

FIG.2 Rotating Disk with filter Set.

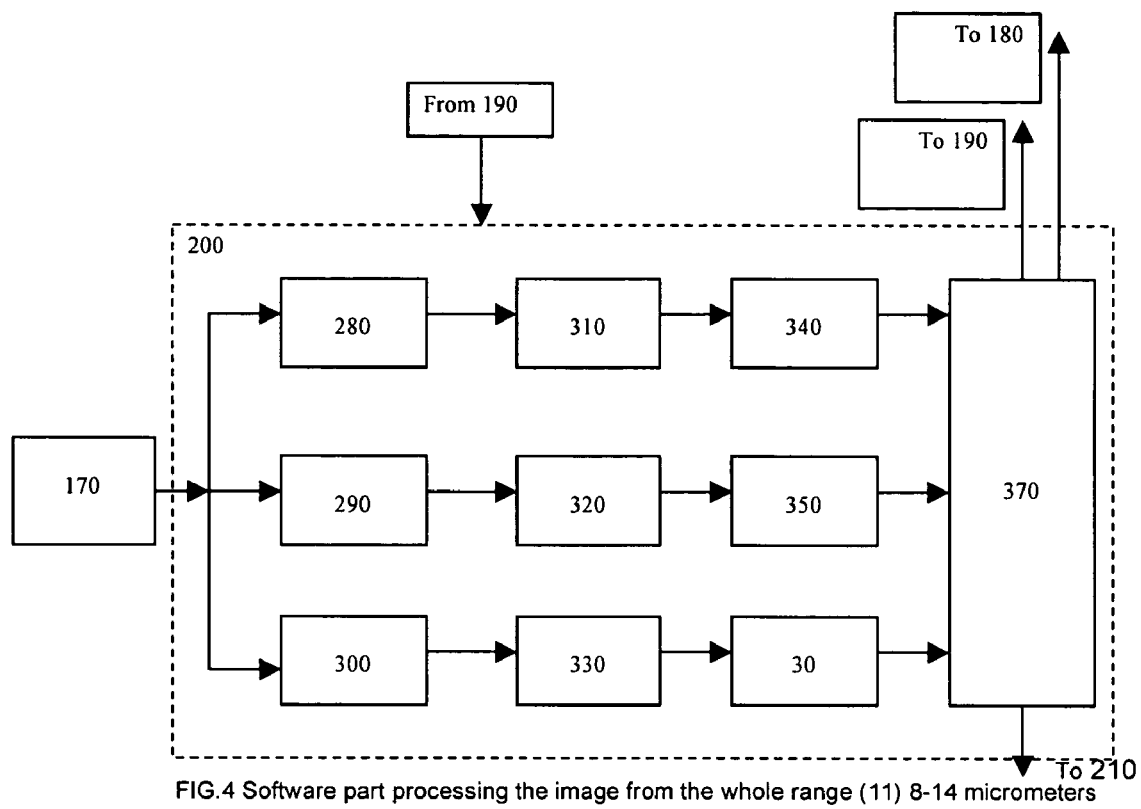
FIG. 4 Software part processing the image from the whole range (11) 8-14 micrometers

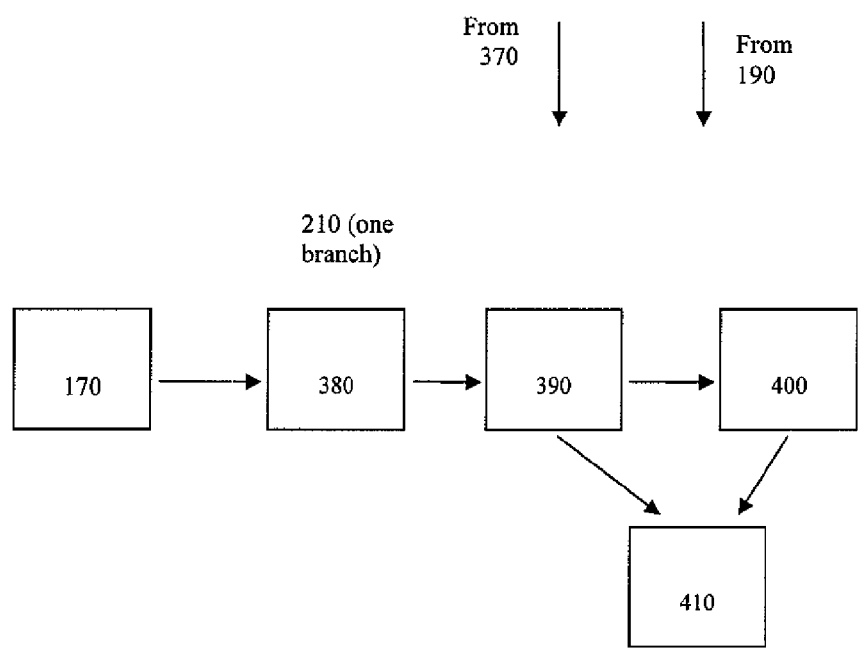
FIG.5a Diagram of one of the branches (220-260) of the set of software filters (210).

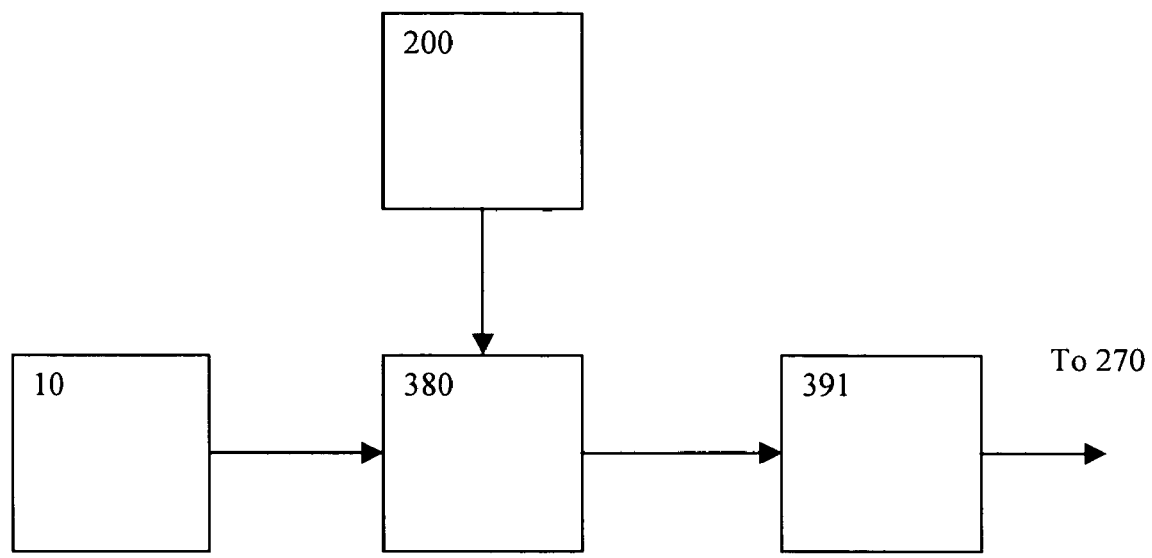
Fig. 5b Embodiment of a branch filter software.

Structural Diagram of the proposed system

METHODS AND SYSTEMS FOR DETECTING PRESENCE OF MATERIALS

CROSS REFERENCE TO RELATED APPLICATIONS

This application claims priority of U.S. Provisional Application Ser. No 60/593,950, filed on Feb. 25, 2005 by Izrail Gorian et al., Infrared Technology for security screening, hereby incorporated by reference.

BACKGROUND OF THE INVENTION

There are several instances in which detection of a predetermined material is desired. One of those instances is the detection of explosives concealed in the body of a person entering a secured area.

Present day personnel inspection systems designed to locate weapons which are employed at the portals of secured areas, e.g. courthouses, military installations and the like, normally rely upon electromagnetic detection of a mass of metallic material. Such systems have been in use in airports for a number of years. However, the limitations of such systems are becoming increasingly significant. Electromagnetic systems are limited to the detection of metallic items such as conventional handguns and therefore cannot detect the plastic and ceramic weapons now being manufactured and sold. Such electromagnetic systems also cannot form an image of the detected material; they merely respond to a mass of the metal passing the detector. Similarly, such systems are incapable of detecting other contraband, such as drugs or certain chemical explosives.

Many proposed systems have relied upon the ability of millimeter waves (radiation of wavelength between one millimeter and one centimeter, that is, between 30-300 GHz frequency) to penetrate clothing without harm to the wearer. Millimeter waves are generally reflected from metallic objects and can be used to form an image of such objects. The attenuation and reflection characteristics of ceramic and plastic weapons, as well as contraband such as narcotics, are different with respect to millimeter-wave radiation from those of skin, so that it is possible, although it has not previously been practical, to form an image of objects of these materials carried by a person. These characteristics render millimeter waves suitable for detection of ceramic weapons or other contraband concealed beneath the clothing, for example, of an individual seeking to enter a secured area. Millimeter wave technology, however, presents privacy issues and typically does not have the speed necessary for applications where the detection system is placed at the portal to a secured area.

Other explosives-detection technologies that are based on x-ray techniques measure the x-ray attenuation of the materials that make up the baggage. A number of techniques utilizing neutrons have been proposed for explosives-detection. However, both x-ray based technologies and a neutron based technologies pose safety hazards when employed to detect concealed materials carried by a human or animal.

Therefore and there is need for systems to detect concealed materials which can be both safe to use on humans and fast enough for applications at portals to secured areas.

It is a further need to provide explosive detection techniques that present fewer privacy issues.

BRIEF SUMMARY OF THE INVENTION

In one embodiment, the system of this invention includes an image acquisition device capable of receiving electromagnetic radiation from an emitting body and of acquiring an image of the emitting body from the received electromagnetic radiation, a filter assembly including a number of filters, the filter assembly disposed between the emitting body and the image acquisition device, each filter from the number of filters in the filter assembly allowing transmission in substantially a predetermined range of wavelengths, one filter from the number of filters being disposed to allow transmission of electromagnetic radiation to the image acquisition device, a feature extraction component capable of identifying at least one region in an image, the feature extraction component being capable of receiving the image from the image acquisition device, the image corresponding to transmission of electromagnetic radiation, emitted by the emitting body, through one filter from the number of filters, an analysis component capable of receiving the at least one region, the analysis component being also capable of obtaining characteristics of the at least one region in at least one predetermined image, the at least one predetermined image corresponding to transmission of electromagnetic radiation, emitted by the emitting body, through at least one predetermined filter from the number of filters, and of providing at least one image of the at least one region in the at least one predetermined image, a database of wavelength spectrum data corresponding to at least one predetermined material, and a detection component capable of receiving the image of the one or more regions of interest in the other predetermined image and the wavelength spectrum data from the database and also capable of detecting presence of the one or more predetermined materials.

Embodiments of methods of detecting presence of at least one predetermined material and computer usable media having computer readable code embodied therein to implement the methods and systems of this invention are also within the scope of this invention.

For a better understanding of the present invention, together with other and further needs thereof, reference is made to the accompanying drawings and detailed description and its scope will be pointed out in the appended claims.

BRIEF DESCRIPTION OF THE DRAWINGS

FIG. 4 is a schematic block diagram representation of an embodiment of a component of the system of this invention;

FIG. 5a is a schematic block diagram representation of an embodiment of another component of the system of this invention;

FIG. 5b is a schematic block diagram representation of another embodiment of another component of the system of this invention;

DETAILED DESCRIPTION OF THE INVENTION

Methods and systems for determining the presence of a predetermined material in a body are disclosed herein below.

Figure 1:
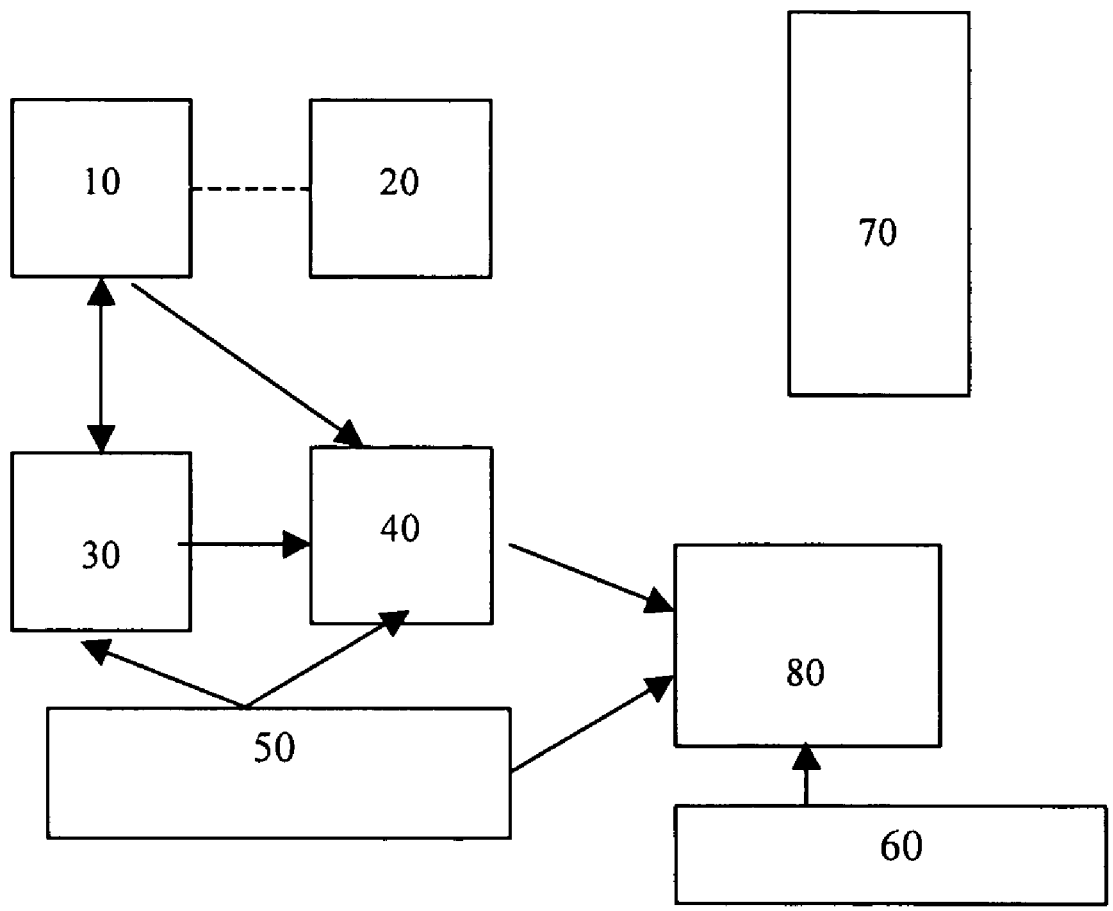
FIG. 1 is a schematic block diagram representation of an embodiment of the system of this invention.

A block diagram representation of an embodiment of the system of this invention is shown in FIG. 1. Referring to FIG. 1, an image acquisition device 10 is located such that the image acquisition device 10 is capable of receiving electromagnetic radiation from an emitting body 70. A filter assembly 20, comprising a number of filters, is disposed between the emitting body 70 and the image acquisition device 10. Each filter from the number of filters in the filter assembly 20 is capable of allowing transmission in substantially a predetermined range of wavelengths. One or more filters from the number of filters are disposed to allow transmission of electromagnetic radiation to the image acquisition device 10. A feature extraction component 30, capable of identifying one or more regions in an image, receives a predetermined image from the image acquisition device 10. The predetermined image corresponds to transmission of electromagnetic radiation, emitted by the emitting body 70, through a predetermined filter from the number of filters. The feature extraction component 30 is capable of classifying one or more identified regions in the predetermined image as being one or more regions of interest in the image of the received electromagnetic radiation from the emitting body 70. An analysis component 40 receives the one or more regions of interest data from the feature extraction component 30 and one or more other predetermined images. The one or more other predetermined images correspond to transmission of electromagnetic radiation from the emitting body 70 through one or more other predetermined filters from the filter assembly 20 and are provided by the image acquisition device 10. The analysis component 40 is also capable of obtaining characteristics of the one or more regions of interest in the one or more other predetermined images and of providing those characteristics and an image of the one or more regions of interest in the one or more other predetermined images. A database 60 includes wavelength spectrum data corresponding to one or more materials. A detection component 80, capable of detecting presence of the one or more materials, receives the image of the one or more regions of interest in the one or more other predetermined images from the analysis component 40 and the wavelength spectrum data from the database 60.

In one embodiment, the system of this invention also includes an adaptive component 50 capable of adjusting parameters of the feature extraction component 30 or/and the analysis component 40 or/and the detection component 80. In one instance, the adaptive component 50 includes a neural network. It should be noted that other embodiments of the adaptive component are also within the scope of this invention. For example, this invention not been deleted just to these examples, the adaptive component 50 can be a component utilizing other artificial intelligence techniques or a component utilizing other optimization techniques.

In one instance, the filter assembly 20 includes a substantially non-attenuating filter and the predetermined image utilized by the feature extraction component 30 corresponds to transmission of electromagnetic radiation through the substantially non-attenuating filter.

Figure 2:
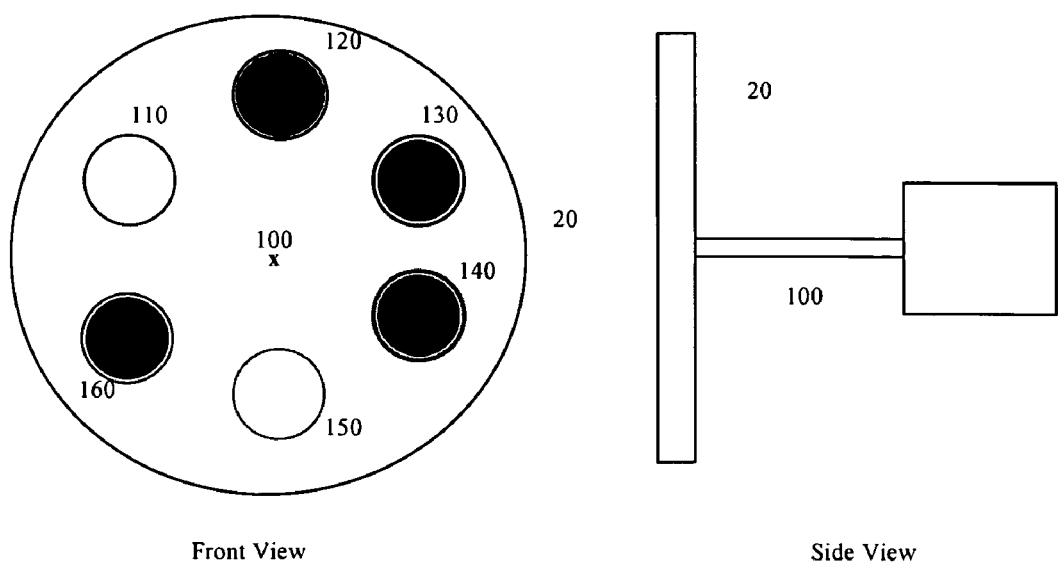
FIG. 2 is a schematic graphical representation of an embodiment of the filter assembly in an embodiment of the system of this invention.
Figure 6:
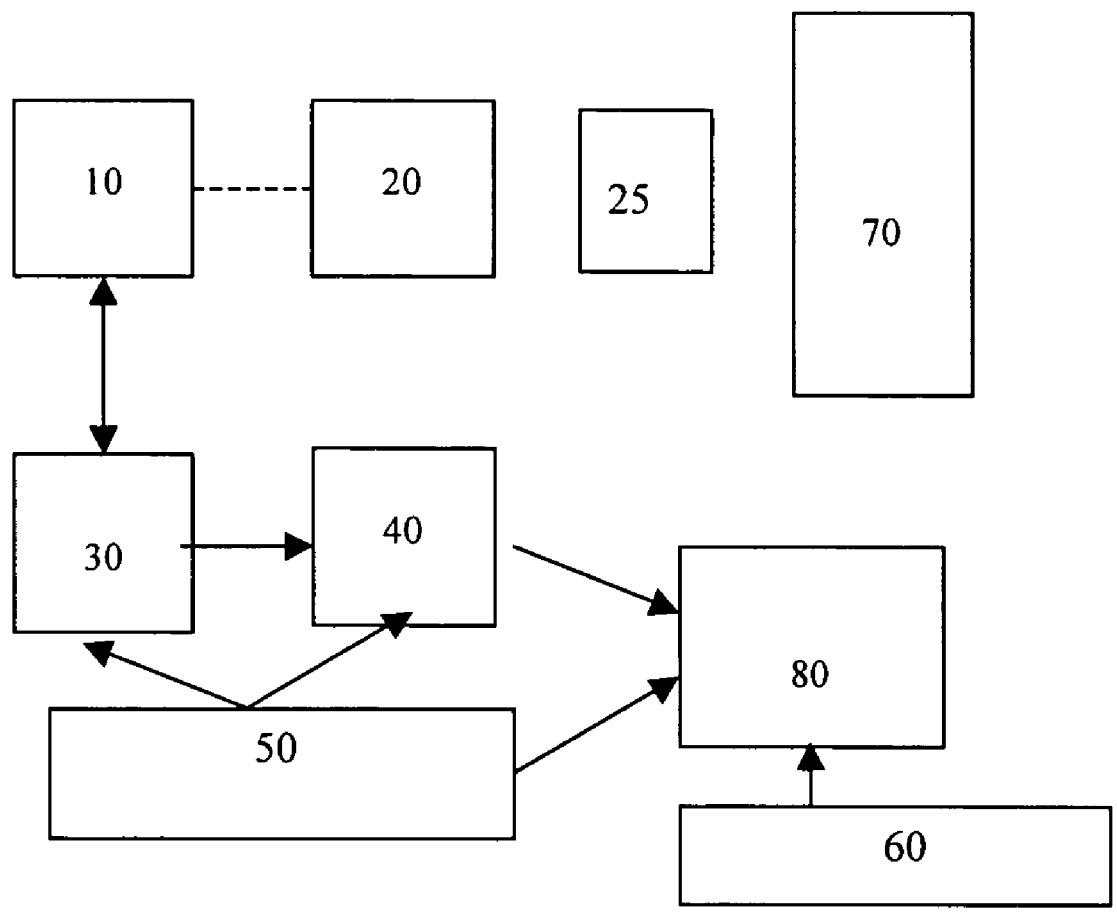
FIG. 6 is a schematic block diagram representation of yet another embodiment of the system of this invention.

One detailed embodiment of the filter assembly 20 is shown in FIG. 2. The embodiment of the filter assembly 20 shown in FIG. 2 includes a disk (wheel) with a set of filters (120 through 160). The disk rotates about the axis 100 placing one of the filters (120 through 160) between the emitting body 70 and the acquisition device 10. Although 5 filters and one non-attenuating filter are shown in FIG. 6, the number of filters is not a limitation of this invention.

In one instance, the wavelength range of interest is the infrared range, from about 1μ to about 15μ. (In another instance, the wavelength range of interest is from 8μ to about 14μ; in yet another instance, the wavelength range of interest is from 3μ to about 5μ.) In one instance, each of the filters can be selected so that it covers a specific narrow range including peaks in the wavelength spectrum data corresponding to one or several predetermined materials. In another instance, the filters are selected so that the group of filters covers an entire wavelength range by substantially equal increments. (For example, if the range of interest is from 8μ to about 14μ, the five filters can be selected such that each filter allows transmission substantially through a band of about 1.2μ and the combination of five filters covers the entire range.) In the embodiment in which the range of wavelengths of interest is in the infrared range, the acquisition device 10 is, in one instance, an infrared digital camera or an infrared sensor that is capable of providing data for a number of pixels.

It should be noted that other embodiments of the filter assembly 20 are within the scope of this invention. For example, an embodiment such as the one described in the US Patent Application Publication No. 2003/0173503 or U.S. Pat. Ser. No. 6,856,466, Multiple imaging system, granted to Michael D. Tocci on Feb. 15, 2005, both of which are incorporated by reference herein, would be within the scope of this invention.

Figure 3:
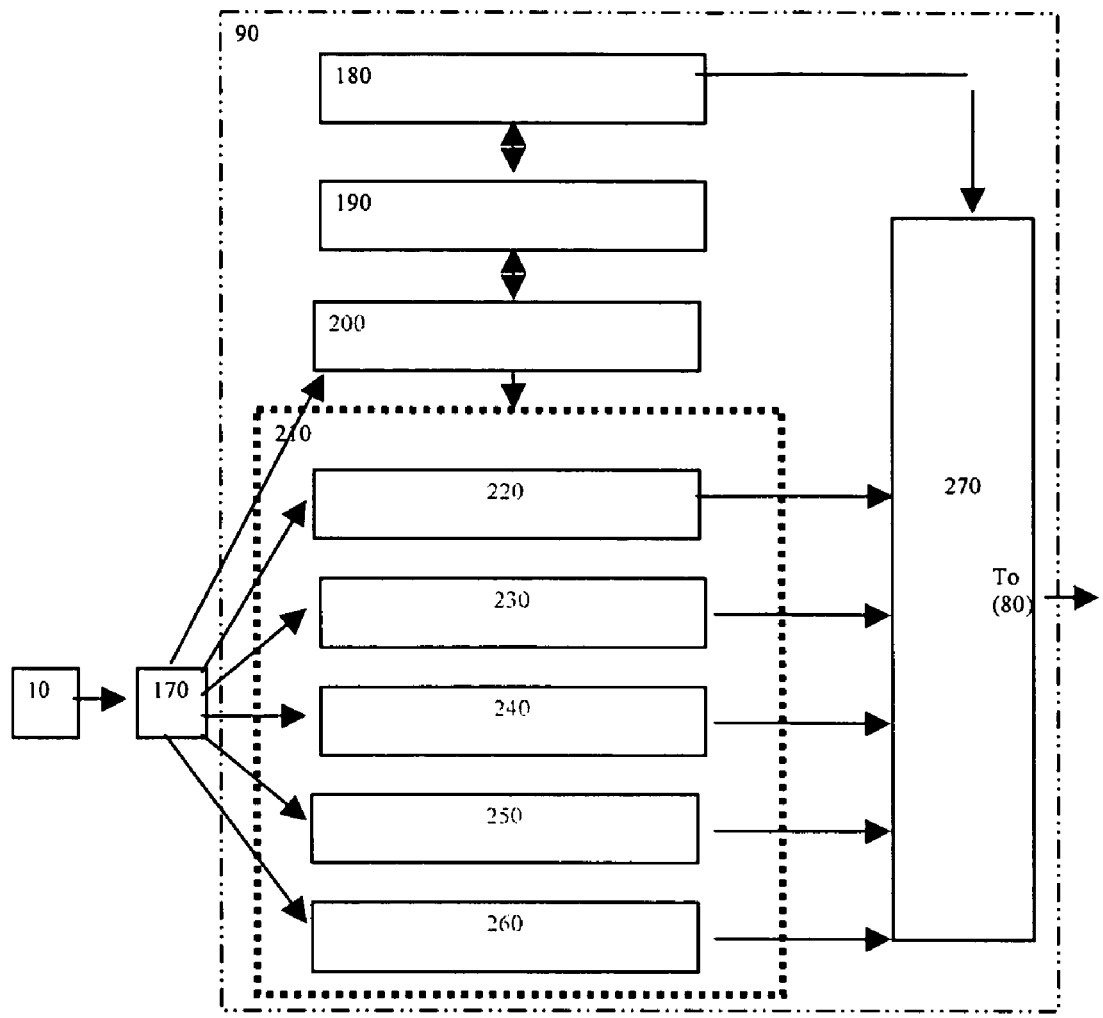
FIG. 3 is a schematic block diagram representation of another embodiment of the system of this invention.

An embodiment of the portion of the system of this invention including the acquisition device 10 and subsequent elements (the feature extraction component 30, the analysis component 40, the adaptive component 50, the detection component 80 and the database 60) is shown in FIG. 3. Referring to FIG. 3, the block labeled 200 represents an embodiment of the feature extraction component (30, FIG. 1) and the block labeled 210 represents an embodiment of the analysis component (40, FIG. 1). The block labeled 190 represents embodiment of the adaptive component (50, FIG. 1). The block labeled 180 represents an embodiment of the database (60, FIG. 1) and the block labeled 270 represents an embodiment of the decision component (80, FIG. 1). In the embodiment shown in FIG. 3, the system of this invention also includes a connection component 170 disposed to receive image data from the image acquisition device 10 and to provide image data to the feature extraction component 200 and the analysis component 210. In one embodiment, the connection component 170 includes a frame grabber; in other embodiments, the connection component 170 is a FireWire interface. It should be noted that many different embodiments of the connection component 170 are within the scope of this invention.

A detailed embodiment of the feature extraction component 200 is shown in FIG. 4. Referring to FIG. 4, in one embodiment, the connection component 170 provides to the feature extraction component 200 the data corresponding to the image data generated by transmission through the substantially non-attenuating and nonselective filter (such as 110 in FIG. 2). In another embodiment, the feature extraction component 200 is incorporated in one or each of the subcomponents of the analysis component 210; in that embodiment, the connection component 170 provides to the feature extraction component the image data generated by transmission through one of the filters, such as filters 120-160 in FIG. 2. The feature extraction component 200 includes a spatial frequency filter bank (280, 290, 300). In one embodiment the spatial filter bank is a wavelet based filter bank. The output of the spatial frequency filter bank (280, 290, 300) is provided to adaptive thresholding subcomponents (310, 320, 330) in order to segment the image data into regions (thereby identifying regions). Labeling subcomponents (340, 350 and 360) provide an identifying label for each region. In one embodiment in the adaptive component 190 includes a neural network. The adaptive component 190 adjusts the parameters of the spatial frequency filter bank (280, 290, 300) and the adaptive thresholding subcomponents (310, 320, 330). (In one instance, the feature extraction component 200 is performing an operation akin to unsupervised segmentation. Wavelet filter banks and neural networks have been applied to unsupervised segmentation. See, for example, Chen, Z., Feng, T. J., Houkes, Z, *Texture segmentation based on wavelet and Kohonen network for remotely sensed images*, 1999 IEEE International Conference on Systems, Man, and Cybernetics, pp. 816-821, vol. 6, 1999, which is incorporated by reference herein, and Hu Chao, Ray, S. R., Nanning Zheng, *Texture segmentation using joint time frequency representation and unsupervised classifier*, 1995 IEEE International Conference on Systems, Man, and Cybernetics, vol.1, Oct. 22-25, 1995, pp. 304-309, which is also incorporated by reference herein.) In the region information and the output of the labeling subcomponents (340, 350 and 360) is provided to a region of interest determining subcomponent 370, which determines which of the identified regions can be classified as regions of interest. The adaptive component 190 (a neural network in one embodiment) is utilized by the region of interest determining subcomponent 370. In one embodiment, the region of interest determining subcomponent 370 can also determine and use shape characteristics in classifying regions as regions of interest.

It should be noted that other spatial frequency filters besides wavelet filter banks are within the scope of this invention. (See for example, T. Randen, J. H Husoy, *Filtering for texture classification: a comparative study*, IEEE Transactions on Pattern Analysis and Machine Intelligence, Vol. 21, Issue 4, April 1999, pp. 291-310, which is incorporated by reference herein.)

It should also be noted that embodiments utilizing other segmentation techniques in order to identify the regions are also within the scope of this invention. (See for example, but not limited to, Ch. 9, Image Segmentation, in Handbook of Pattern Recognition and Image Processing, ISBN 0-121-774560-2, which is incorporated by reference herein, C. Kervrann and F. Heitz, "A Markov random field model based approach to unsupervised texture segmentation using local and global spatial statistics," IEEE Transactions on Image Processing, vol. 4, no. 6, 1995, 856-862. citeseer.ist.psu.edu/kervrann93markov which is incorporated by reference herein, and S. Liapis and E. Sifakis and G. Tziritas, "Colour and Texture Segmentation Using Wavelet Frame Analysis, Deterministic Relaxation, and Fast Marching Algorithms," citeseer.ist.psu.edu/liapis04colour, which is also incorporated by reference herein.)

It should also be noted that a variety of adaptive thresholding methods are within the scope of this invention. (For adaptive thresholding, see, for example, but not limited to, ø.D. Trier and T. Taxt, Evaluation of binarization methods for document images, available at citeseer.nj.nec.com/trier95evaluation, also a short version published in IEEE Transaction on Pattern Analysis and Machine Intelligence, 17, pp. 312-315, 1995, both of which are incorporated by reference herein.)

It should also be noted that embodiments of the feature extraction component that do not have a region of interest determining subcomponent 370 are also within the scope of this invention. In those embodiments, the identified regions are the regions of interest. Therefore, in the description below, the term "identified region" is used to denote the output of the feature extraction component 200.

One embodiment of the analysis component 210 is shown in FIG. 5*a*. FIG. 5*a* depicts one of the subcomponents (220 through 260) of the analysis component 210. The structure of each of the subcomponents (220 through 260) is similar; each subcomponent operates on an image corresponding to transmission of electromagnetic radiation from the emitting body 70 through one predetermined filter (in one embodiment, the image that the subcomponent 220-260 operates on is the friend from the image utilized by the feature extraction component 200; in another embodiment, the image that the subcomponent 220-260 operates on is the same as the image that the feature extraction component 200 operated on)from the filter assembly 20. The embodiment of the subcomponent shown in FIG. 5*a* includes an image extraction subcomponent 380, a measuring subcomponent 390, another measuring subcomponent 400, and a decision subcomponent 410. (In one embodiment, the feature extraction component 200 operates under the same image as that used by each of the analysis subcomponent 220-260.) The image extraction subcomponent 380 receives data and labels for one or more regions from the feature extraction component 200 and provides an extracted image of each received region in the image corresponding to transmission through the predetermined filter. (Each region can be considered a "mask" and only the portion of the image corresponding to transmission through the predetermined filter that is under the "mask" is analyzed.) Each extracted image has a label (the region label received from the feature extraction component 200) associated with it. In one embodiment, the image extraction subcomponent 380 provides the extracted image of each received region to the measuring subcomponent 390 and the other measuring subcomponent 400. (Embodiments in which the analysis of subcomponent does not include the measuring subcomponents in 90 and the other measuring subcomponent 400 are also within the scope of this invention. In the embodiment shown in FIG. 5*a*, the feature extraction component 200 can provide just the regions and the label for each region and the measuring subcomponents 380, 400 and the decision subcomponent 410 can be used to determine whether a region should be further analyzed.) The measuring subcomponent 380 determines physical characteristics (such as, but not limited to, image intensity or image density) for each extracted image. The other measuring subcomponent 400 determines shape characteristics for each extracted image. In one instance, the shape characteristics include area and moment invariants. (The moment invariants can be used to classify the shape. See, for example, Ezer, N., Anarim, E., Sankur, B, *A comparative study of moment invariants and Fourier descriptors in planar shape recognition*, Proceedings of 7th Mediterranean Electrotechnical Conference, 1994, 12-14 Apr. 1994, pp. 242-245, vol.1, which is incorporated by reference herein. Embodiments of other than those utilizing moment invariants are also within the scope of this invention.) The physical characteristics and the shape characteristics for each region are provided to the decision subcomponent 410. The decision subcomponent 410 determines which of the regions are of interest for further investigation and provides the images of those regions to the final decision component 270. The parameters of the measuring subcomponents 390,400 are adjusted with assistance from the adaptive component 190 (one or more neutral networks in one embodiment). The determination of whether a region (and the image of the region) is of interest for further investigation is also performed with the assistance of the adaptive component 190 (one or more neutral networks in one embodiment).

Another embodiment of the analysis subcomponent 220-260 is shown in FIG. 5*b*. Referring to FIG. 5*b*, the acquisition component 10 provides data for an image corresponding to transmission of electromagnetic radiation from the emitting body 70 through one predetermined filter to the image extraction subcomponent 380. (In this embodiment, the connection subcomponent 170 is incorporated into the image acquisition component 10.) The feature extraction component 200 provides data and labels for one or more regions. The image extraction subcomponent 380, as described above, provides the extracted image of each received region. In the embodiment shown in FIG. 5b, the extracted image of each received region is provided to the noise reduction component 391. The noise reduction components 391, in the embodiment shown, accumulate pixel values within each received region. It should be noted that other known reduction components, such as but not limited to, wavelet denoising, or noise reduction filters, are within the scope of this invention. (Not desiring to be bound by theory, one explanation of the operation of embodiment of the noise reduction component described above relies on the fact that, while signal adds linearly when accumulated, noise adds as the root mean square. Still not desiring to be bound by theory, in another explanation of the operation of the embodiment of the noise reduction component, the embodiment of the noise reduction components presented above can be considered a low pass filter.)

Another embodiment of the system of this invention is shown in FIG. 6. Referring to FIG. 6, the embodiment shown therein also includes another filter assembly 25 comprising another number of filters, the other filter assembly 25 being disposed between the emitting body 70 and the filter assembly 20. Each filter from the other number of filters in the other filter assembly 25 is capable of allowing transmission in substantially a predetermined polarization.

During use of the embodiment of the system of this invention, detecting the presence of selected materials in the emitting body (typically concealed under a cover of the emitting body, but this invention is not limited only to that application) includes acquiring a number of images, where each image corresponds to received electromagnetic radiation in substantially a predetermined range of wavelengths, each predetermined range being different. (Embodiments in which at least two of the ranges overlap are within the scope of this invention.) One or more regions are identified from a predetermined image. And identifying label is provided for in each one of the regions. (Typically, the image used to identify the one or more regions is the image obtained when a substantially non-attenuating filter, or a clear filter, is used. However, this invention is not limited to this typical embodiment.) Using each of the one or more regions as a "mask," an image of each region is obtained from an image corresponding to transmission through each of the other filters. Applying the region as a mask, extracted images are obtained. Physical and shape characteristics are obtained for each extracted image. The physical characteristics can include intensity or density. Shape characteristics can include area and moment invariants. The physical and shape characteristics can be used to determine whether the extracted image should be analyzed further. The extracted images of each region resulting from having applied the region as a mask, after deciding that the extracted image should be further analyzed, are compared to wavelength spectrum data obtained from a database.

Figure 7:
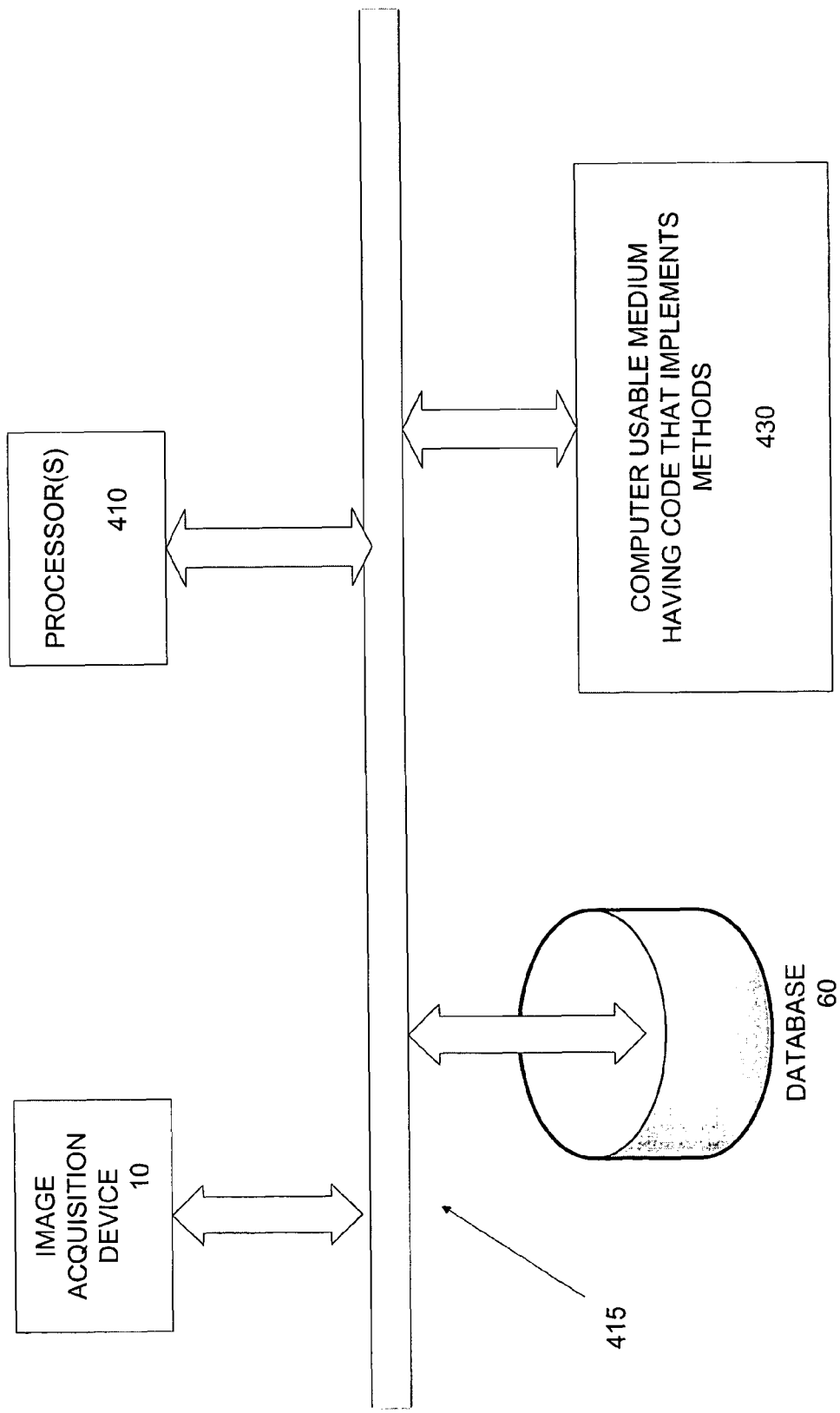
FIG. 7 is a schematic block diagram representation of an embodiment of several components of the system of this invention.

In one embodiment, the feature extraction component 30, the analysis component 40, the adaptive component 50, and the detection component 70 are implemented as computer readable code (software) embodied in a computer usable medium. The noise reduction component 170 can also be implemented as computer readable code embodied in a computer usable medium. FIG. 7 shows an embodiment of components of the system of this invention. As shown in FIG. 7, the acquisition device 10 is operatively connected to one or more processors 410, one or more computer usable media 420, and a database 60. The computer readable code embodied in the one or more computer usable media 420 is capable of causing the one or more processors 410 to execute the methods of this invention or implement the systems of this invention. The acquisition device 10, the one or more processors 410, the database 60 and the computer usable medium 420 are operatively connected by means of a connection component 415 (the connection component may be, for example, a computer bus, or a carrier wave).

In one instance, the computer readable code is capable of causing a computer system (the one or more processors 410) to receive a predetermined image from the image acquisition device 10, identify at least one region in the predetermined image, obtain one or more extracted images in at least another predetermined image also obtained from the image acquisition device 10, obtain wavelength spectrum data from the database 60 and detect presence of at least one material from the one or more extracted images and the wavelength spectrum data. In one embodiment, in being capable of causing the computer system to identify at least one region, the computer readable code is capable of causing the computer system to filter the predetermined image utilizing a spatial frequency filter bank and adaptively threshold the filtered predetermined image. In one embodiment, the computer readable code is also capable of causing the computer system to adjust parameters of the spatial frequency filter bank. In another embodiment, the computer readable code is also capable of causing the computer system to adjust the adaptive thresholds. In one instance, the adjustments are performed by a neural network. In one embodiment, the computer readable code is also capable of causing the computer system to providing an identifying label corresponding to a predetermined region. In one instance, the computer readable code is also capable of causing the computer system to classify at least one identified region as being of interest. In one embodiment, the computer readable code, in obtaining the at least one extracted image in the at least another predetermined image, is capable of causing the computer system to provide the at least one extracted image of the at least one region in the at least another predetermined image, determine physical characteristics of the at least one extracted image, and determine shape characteristics of the at least one extracted image. In one instance, the computer readable code is also capable of causing the computer system to compare the at least one extracted image, corresponding to received electromagnetic radiation in substantially a different predetermined range of wavelengths, to the wavelength spectrum data.

In order to better describe the methods and systems of this invention, the following exemplary embodiment is described herein below. One exemplary embodiment of the methods and systems of this invention is described hereinbelow in which the body 70 is a human body and the object is concealed under cloth. It should be noted that other embodiments are within the scope of this invention.

In the embodiment presented below, thermal body radiation (heat) emanates from an investigated person and is received by an infrared camera 10. The infrared camera 10 can be stationary, remotely controlled or controlled by operator. The infrared Camera 10 generates an image. The Infrared camera 10 provides an image signal to the computer system as shown in FIG. 7. The image signal is analyzed, by means of computer readable code (software) embodied in a computer usable medium 420, in order to detect the presence of objects concealed under cloth on the investigated person. The computer system 410 and the computer readable code represent an embodiment of the feature extraction component, the analysis component and the detection component, such as the embodiment shown in FIGS. 3, 4, 5.

Fortuitously, the emissivity spectra for a compound material (a mixture), such as cotton fabric over polyethilene, is obtained by adding together in a simple linear fashion the emissivity spectra of the individual components of a compound material. The emissivity spectra can be converted to an infrared signature (a thermal signature). (The thermal signature is the apparent temperature for a given wavelength band. The apparent temperature of a surface is the temperature of a blackbody source having the same radiant emittance, averaged over a specified waveband, as the radiant emittance of the surface averaged over the same wavelength band.) In the exemplary embodiment, the filter assembly includes a number of filters, where each filter covers a wavelength band of interest. One of the filters is an un-attenuating or clear filter, which is used by the feature extraction component to obtain one or more regions. The physical characteristics of the extracted images of each region (extracted from the image resulting from transmissions through one of the filters, other than the unattenuating filter) resulting from having applied the region as a mask can be expressed in terms of an apparent temperature. Each extracted image, corresponding to a wavelength band, can be compared to a thermal signature.

Figure 8:
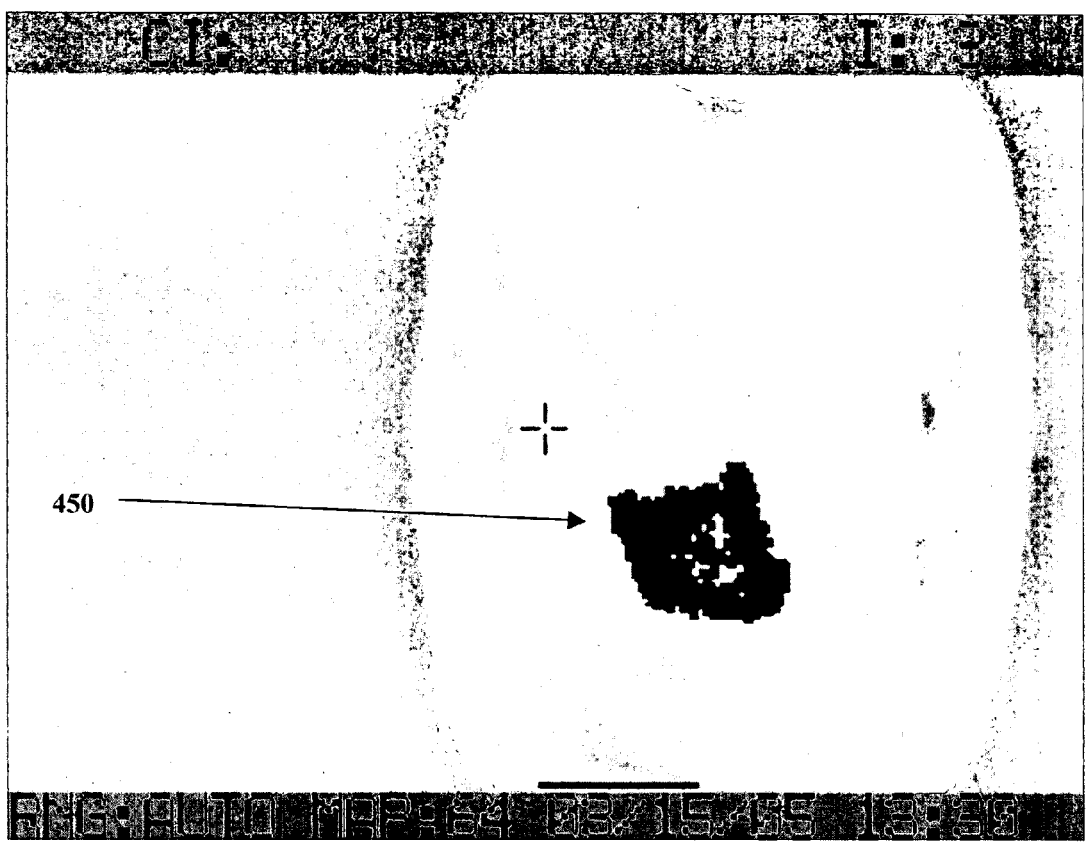
FIGS. 8-10 are pictorial representations of output from an exemplary embodiment of the system of this invention.
Figure 9:
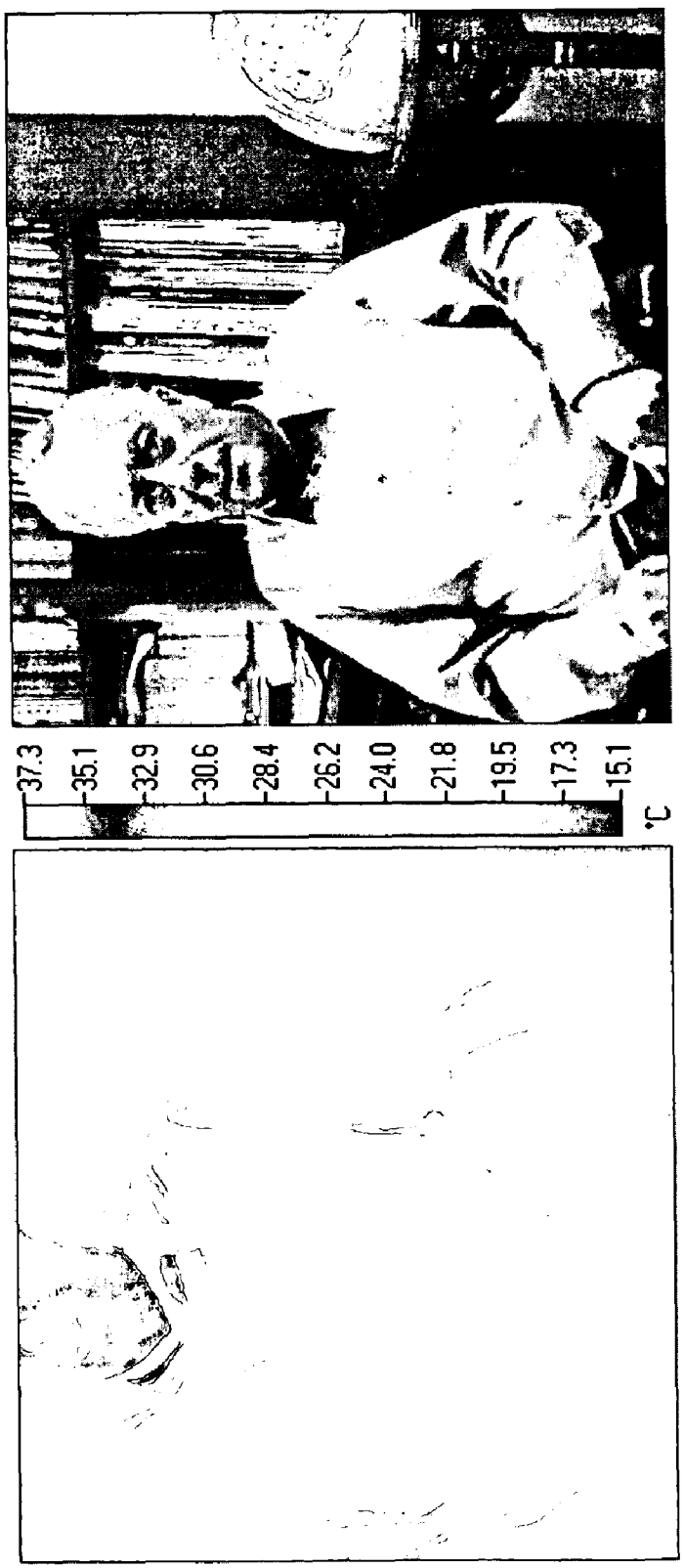
Figure 10:
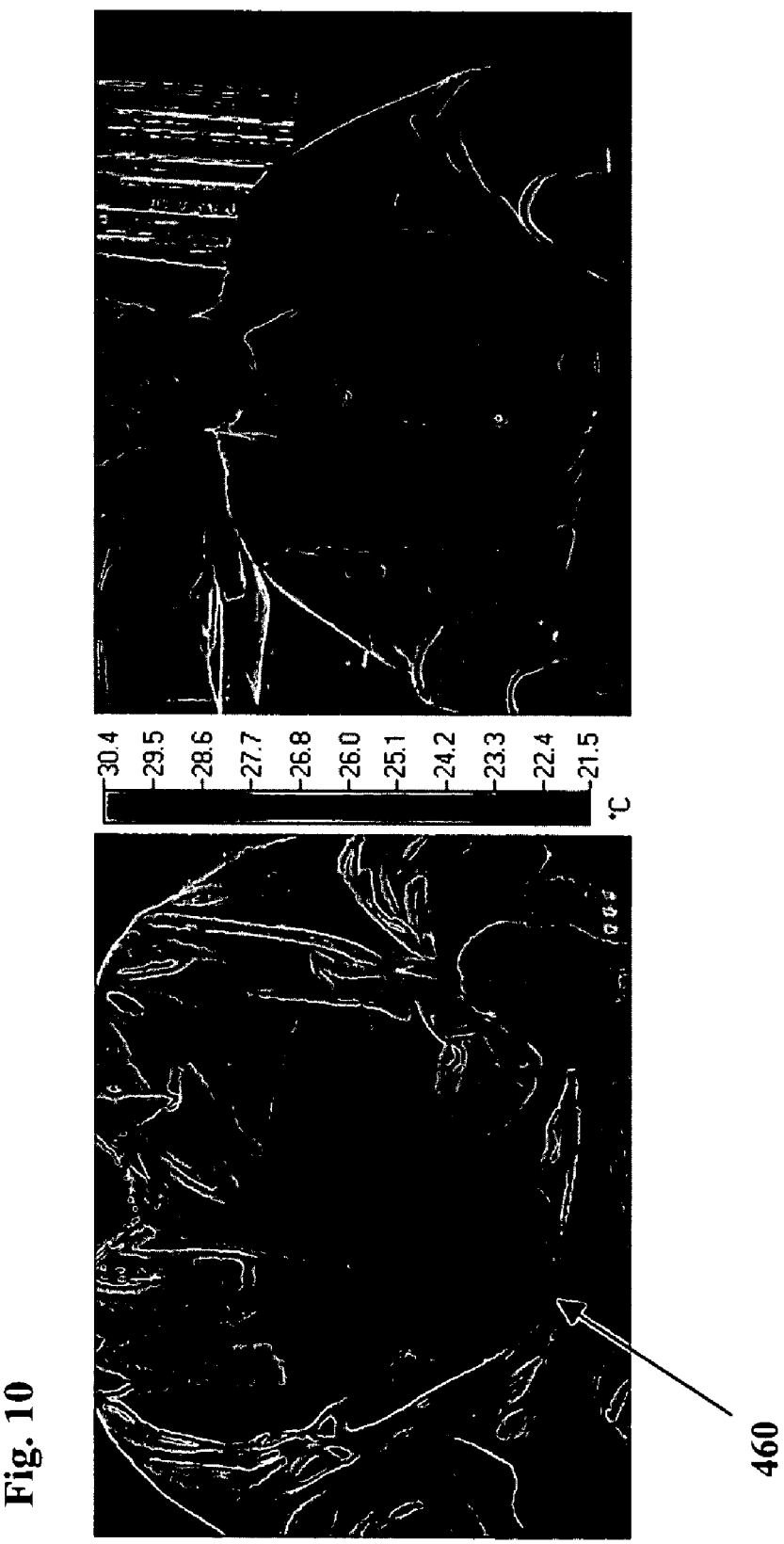

FIG. 8 shows an image of a detected object 450 that is concealed under cloth. FIG. 9 shows an image of a body in which there are no concealed objects. FIG. 10 shows an image of a detected plastic plate, where the plastic plate was concealed under cloth.

It should be noted that other embodiments, besides the above described exemplary embodiment, are also within the scope of this invention.

The techniques described above may be implemented in one or more computer programs executing on a programmable computer including a processor, a storage medium readable by the processor (including, for example, volatile and non-volatile memory and/or storage elements), and, in some embodiments, also including at least one input device, and/or at least one output device. Program code may be applied to data entered using the input device (or user interface) to perform the functions described and to generate output information. The output information may be applied to one or more output devices.

Elements and components described herein may be further divided into additional components or joined together to form fewer components for performing the same functions.

Each computer program (computer readable code) may be implemented in any programming language, such as assembly language, machine language, a high-level procedural programming language, an object-oriented programming language, or a combination thereof. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable (computer usable) media include, for example, a floppy disk, a flexible disk, hard disk, magnetic tape, or any other magnetic medium, a CDROM, any other optical medium, punched cards, paper tape, any other physical medium with patterns of holes or other patterns, a RAM, a PROM, and EPROM, a FLASH-EPROM, any other memory chip or cartridge, a carrier wave, such as electromagnetic radiation or electrical signals, or any other medium from which a computer can read.

Although the invention has been described with respect to various embodiments, it should be realized this invention is also capable of a wide variety of further and other embodiments within the spirit and scope of the appended claims.

What is claimed is:

1. A system for detecting the presence of selected materials, the system comprising:

an image acquisition device receiving electromagnetic radiation from an emitting body and acquiring an image of the emitting body from the received electromagnetic radiation;

a filter assembly comprising a plurality of filters, said filter assembly disposed between the emitting body and said image acquisition device; each filter from said plurality of filters in said filter assembly allowing transmission in substantially a predetermined range of wavelengths, one filter from said plurality of filters being disposed to allow transmission of electromagnetic radiation to said image acquisition device;

a feature extraction component, said feature extraction component identifying at least one region in said image, said feature extraction component receiving said image of the emitting body from said image acquisition device, said image of the emitting body corresponding to transmission of electromagnetic radiation, emitted by the emitting body, through one filter from said plurality of filters;

an analysis component receiving said at least one region, said analysis component obtaining characteristics of said at least one region in at least one predetermined image, said at least one predetermined image corresponding to transmission of electromagnetic radiation, emitted by the emitting body, through at least one predetermined filter from said plurality of filters, and providing at least one output image of said at least one region in said at least one predetermined image; said at least one output image being at least one image of a region of interest for detecting presence of predetermined materials;

a database of wavelength spectrum data corresponding to at least one material from said predetermined materials; said predetermined materials comprising explosives; and a detection component receiving said at least one output image of said least one region in said at least one predetermined image from said analysis component and the wavelength spectrum data from said database and also detecting presence of said at least one material by comparing said at least one image of said at least one region to the wavelength spectrum data.

2. The system of claim 1 wherein at least some of said received electromagnetic radiation is in the range of about 1μ to about 14μ.

3. system of claim 2 wherein at least some of said received electromagnetic radiation is in The range of about 8μt to about 14μ.

4. The system of claim 2 wherein at least some of said received electromagnetic radiation is in the range of about 3μto about 5μ.

5. The system of claim 1 wherein said image of the emitting body is another predetermined image, said another predetermined image corresponding to transmission of electromagnetic radiation from the emitting body through another predetermined filter from said plurality of filters.

6. The system of claim 5 wherein another filter from said plurality of filters is a substantially non-attenuating filter.

7. The system of claim 1 further comprising an adaptive component adjusting parameters of said feature extraction component.

8. The system of claim 7 wherein said adaptive component also adjusts parameters of said analysis component.

9. The system of claim 7 wherein said adaptive component also adjusts parameters of said detection component.

10. The system of claim 7 wherein said adaptive component comprises a neural network.

11. The system of claim 1 wherein said feature extraction component comprises a spatial frequency filter bank.

12. The system of claim 11 wherein said spatial frequency filter bank comprises a wavelet based filter bank.

13. The system of claim 1 wherein said feature extraction component comprises:
   a labeling subcomponent providing a identifying label corresponding to a predetermined region.

14. The system of claim 1 wherein said analysis component comprises:
   an image extraction subcomponent providing at least one extracted image of said at least one region in said at least one predetermined image;
   a measuring subcomponent determining physical characteristics of said at least one extracted image; and
   another measuring subcomponent determining shape characteristics of said at least one extracted image.

15. The system of claim 14 wherein said physical characteristics comprise intensity.

16. The system of claim 14 wherein said characteristics comprise moment invariants.

17. The system of claim 1 wherein said wavelength spectrum comprises infrared signature data.

18. The system of claim 1 further comprising another filter assembly, said another filter assembly comprising another plurality of filters, said another filter assembly being disposed between the emitting body and said acquisition device; each filter from said another plurality of filters in said another filter assembly being capable of allowing transmission in substantially a predetermined polarization.

19. The system of claim 1 further comprising a noise reduction component receiving image data from said image acquisition device, providing image data to said feature extraction component and said analysis component and of improving signal to noise ratio in said image data.

20. The system of claim 1 wherein said characteristics comprise moment invariants.

21. A method for detecting the presence of selected materials, the selected materials including explosives, the method comprising the steps of:
   acquiring a plurality of images, each of the plurality of images corresponding to received electromagnetic radiation in substantially a different predetermined range of wavelengths;
   identifying at least one region from one image from the plurality of images;
   detecting, from comparing an image of said at least one region in a predetermined image from the plurality of images to wavelength spectrum data corresponding to characteristics of predetermined materials, the predetermined materials including explosives, presence of at least one material from the predetermined materials.

22. The method of claim 21 further comprising the step of obtaining wavelength spectrum data corresponding to characteristics of at least one predetermined material, said at least one predetermined material including explosives.

23. The method of claim 22 wherein said at least one predetermined material comprise at least one composite material.

24. The method of claim 21 wherein the wavelength spectrum data comprises infrared signature data.

25. The method of claim 21 wherein the step of obtaining at least one region comprises the step of:
   providing an identifying label corresponding to a predetermined region.

26. The method of claim 21 wherein the step of detecting the presence of at least one material comprises the steps of:
   providing at least one extracted image of said at least one region in said at least another predetermined image;
   determining physical characteristics of said at least one extracted image; and
   determining shape characteristics of said at least one extracted image.

27. The method of claim 26 wherein said physical characteristics comprise intensity.

28. The method of claim 26 wherein the step of detecting the presence of at least one material further comprises the step of comparing said at least one extracted image corresponding to received electromagnetic radiation in substantially a different predetermined range of wavelengths to said wavelength spectrum data.

29. The method of claim 28 wherein the step of detecting the presence of at least one material further comprises the step of comparing said at least one extracted image to said wavelength spectrum data.

30. The method of claim 21 wherein the step of detecting the presence of at least one material comprises the steps of:
   providing at least one extracted image of said at least one region in said predetermined image;
   determining physical characteristics of said at least one extracted image; and
   determining shape characteristics of said at least one extracted image.

31. A computer usable medium having computer readable code embodied therein, said computer readable code causing a computer system to:
   receive a predetermined image from an image acquisition device;
   identify at least one region in said predetermined image;
   obtain at least one extracted image of said at least one region;
   obtain wavelength spectrum data from a database; and
   detect presence of at least one material from predetermined materials, the predetermined materials including explosives, from said at least one extracted image and said wavelength spectrum data.

32. The computer usable medium of claim 31 wherein said computer readable code, in causing said computer system to identify at least one region, is capable of causing said computer system to:
   filter said predetermined image utilizing a spatial frequency filter bank; and
   adaptively threshold said filtered predetermined image.

33. The computer usable medium of claim 32 wherein said computer readable code also causes said computer system to adjust parameters of said spatial frequency filter bank.

34. The computer usable medium of claim 33 wherein said computer readable code also causes said computer system to apply a neural network to adjust parameters of said spatial frequency filter bank.

35. The computer usable medium of claim 32 wherein said computer readable code also causes said computer system to adjust said adaptive thresholds.

36. The computer usable medium of claim 32 wherein said computer readable code also causes said computer system to apply a neural network to adjust said adaptive thresholds.

37. The computer usable medium of claim 32 wherein said computer readable code also causes said computer system to providing an identifying label corresponding to a predetermined region.

38. The computer usable medium of claim 37 wherein said wavelength spectrum data comprises infrared signatures.

39. The computer usable medium of claim 31 wherein said computer readable code also causes said computer system to classify at least one identified region as being of interest.

40. The computer usable medium of claim 31 wherein said computer readable code, in obtaining said at least one extracted image causes said computer system to:
 determine physical characteristics of said at least one extracted image; and
 determine shape characteristics of said at least one extracted image.

41. The computer usable medium of claim 40 wherein said computer readable code also causes said computer system to:
 decide, utilizing said physical characteristics and said shape characteristics in a decision algorithm, to analyze said at least one extracted image.

42. The computer usable medium of claim 41 wherein said decision algorithm comprises a neural network.

43. The computer usable medium of claim 41 wherein said computer readable code also causes said computer system to:
 compare said at least one extracted image,, corresponding to received electromagnetic radiation in substantially at least one predetermined range of wavelengths, to said wavelength spectrum data.

44. The computer usable medium of claim 31 wherein said computer readable code also causes said computer system to improve signal to noise ratio in said predetermined image.

45. The computer usable medium of claim 44 wherein, in improving signal to noise ratio, said computer readable code causes said computer system to accumulate data from said predetermined image.

46. The computer usable medium of claim 31 wherein said computer readable code, in obtaining said at least one extracted image causes said computer system to:
 provide said at least one extracted image of said at least one region in at least another predetermined image;
 determine physical characteristics of said at least one extracted image; and
 determine shape characteristics of said at least one extracted image.

47. The computer usable medium of claim 46 wherein said computer readable code also causes said computer system to:
 decide, utilizing said physical characteristics and said shape characteristics in a decision algorithm, to analyze said at least one extracted image.

48. The computer usable medium of claim 47 wherein said decision algorithm comprises a neural network.

49. The computer usable medium of claim 47 wherein said computer readable code also causes said computer system to:
 compare said at least one extracted image, corresponding to received electromagnetic radiation in substantially a different predetermined range of wavelengths, to said wavelength spectrum data.

50. The computer usable medium of claim 49 wherein said wavelength spectrum data comprises infrared signatures.

* * * * *

UNITED STATES PATENT AND TRADEMARK OFFICE
CERTIFICATE OF CORRECTION

| | | |
|---|---|---|
| PATENT NO. | : 7,709,796 B2 | Page 1 of 1 |
| APPLICATION NO. | : 11/348121 | |
| DATED | : May 4, 2010 | |
| INVENTOR(S) | : Izrail Gorian et al. | |

It is certified that error appears in the above-identified patent and that said Letters Patent is hereby corrected as shown below:

In column 10, line 56 (claim 2), "14μ" should read -- 15μ --

In column 10, line 48 (claim 3), "8μt to" should read -- 8μ to --

In column 10, line 62 (claim 4), "13μto" should read -- 13μ to --

Signed and Sealed this

Fifteenth Day of June, 2010

David J. Kappos
*Director of the United States Patent and Trademark Office*